United States Patent [19]

Adams et al.

[11] 3,978,226

[45] Aug. 31, 1976

[54] XANTHEN DERIVATIVES SUCH AS N,N'-DIMETHYL-N-9-XANTHENYLUREA AND THE LIKE IN ANTI-SECRETORY COMPOSITIONS, AND METHOD OF TREATING THEREWITH

[75] Inventors: Stuart Sanders Adams; Bernard John Armitage; Norman William Bristow; Bernard Vincent Heathcote, all of Nottingham, England

[73] Assignee: The Boots Company Limited, Nottingham, England

[22] Filed: Feb. 13, 1975

[21] Appl. No.: 549,535

Related U.S. Application Data

[60] Division of Ser. No. 408,378, Oct. 23, 1973, Pat. No. 3,927,029, which is a continuation of Ser. No. 191,112, Oct. 20, 1971, abandoned, which is a continuation-in-part of Ser. No. 662,587, Aug. 23, 1967, Pat. No. 3,644,420.

[30] Foreign Application Priority Data

Sept. 2, 1966   United Kingdom............... 39384/66
Apr. 5, 1967    United Kingdom............... 15692/67

[52] U.S. Cl. ............................................... 424/283
[51] Int. Cl.$^2$........................................ A61K 31/35
[58] Field of Search..................................... 424/283

[56] References Cited
UNITED STATES PATENTS
3,481,930   12/1969   Childress et al. ............... 424/283 X Primary Examiner—Frederick E. Waddell
Attorney, Agent, or Firm—Gordon W. Hueschen

[57] ABSTRACT

N-alkyl-N-9-xanthenylurea and substituted derivatives thereof useful in the treatment of peptic ulcer.

12 Claims, No Drawings

XANTHEN DERIVATIVES SUCH AS N,N'-DIMETHYL-N-9-XANTHENYLUREA AND THE LIKE IN ANTI-SECRETORY COMPOSITIONS, AND METHOD OF TREATING THEREWITH

This application is a division of U.S. application Ser. No. 408,378 filed Oct. 23, 1973, now U.S. Pat. No. 3,927,029, issued Dec. 16, 1975, which is a continuation of U.S. application Ser. No. 191,112 filed Oct. 20, 1971, now abandoned, which in turn is a continuation-in-part of U.S. application Ser. No. 662,587 filed Aug. 23, 1967, now U.S. Pat. No. 3,644,420 issued Feb. 22, 1972.

According to the present invention there are provided compounds of formula I

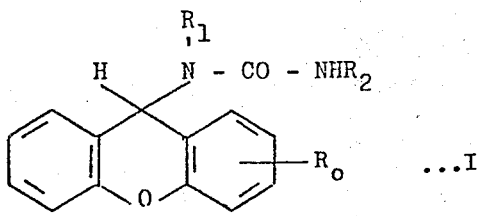

in which
$R_o$ is hydrogen, halogen, alkyl or alkoxy;
$R_1$ is alkyl; and
$R_2$ is hydrogen, alkyl, hydroxyalkyl, alkanoyloxyalkyl, alkoxyalkyl or alkanoyl; and
wherein the terms "alkyl", "alkoxy", "alkanoyloxy" and "alkanoyl" indicate such groups containing up to 7 carbon atoms.

Methods for the preparation of the compounds of formula I are described in detail in our aforementioned U.S. patent application Ser. No. 662,587.

It has been found that the compounds of formula I are antisecretory agents, with a specific activity against gastric secretion and without any anticholinergic activity. The anti-secretory activity has been demonstrated in the stimulated, pylorus-ligated rat, and varies with the values of $R_o$, $R_1$ and $R_2$.

The compounds of the invention may be administered orally, rectally or parenterally, preferably orally, the optimum dosage rate varying with the activity of the compounds. A preferred dosage rate for oral administration is of the order of 0.025–2 g. daily, optionally in divided doses.

In use, the compounds of the invention are administered in conventional formulations, and therefore, according to a further aspect of the invention there are provided therapeutic compositions which comprise a compound of the hereinbefore described formula I in association with pharmaceutical excipients known for the production of compositions suitable for oral, rectal or parenteral administration.

The compositions of the invention preferably contain 0.1 – 90% by weight of a compound of formula I.

Compositions for oral administration are the preferred compositions of the invention, and these are the known pharmaceutical forms for such administration, such as for example tablets, capsules, syrups and aqueous and oily suspensions. The excipients used in the preparation of these compositions are the excipients known in the pharmacist's art. Preferred compositions are tablets wherein a compound of formula I is mixed with an inert diluent such as calcium phosphate in the presence of disintegrating agents e.g. maize starch and lubricating agents e.g. magnesium stearate. Such tablets may, if desired, be provided with enteric coatings by known methods, for example by the use of cellulose acetate phthalate. Similarly capsules, for example hard or soft gelatin capsules, containing a compound of formula I, with or without other excipients, may be prepared by conventional means and, if desired, provided with enteric coatings in known manner. The tablets and capsules may conveniently each contain 25 – 500 mg. of a compound of formula I. Other compositions for oral administration include for example aqueous suspensions containing a compound of formula I in aqueous media in the presence of a non-toxic suspending agent e.g. sodium carboxymethylcellulose and dispersing agents, and oily suspensions containing a compound of formula I in a vegetable oil for example arachis oil.

Compositions of the invention suitable for rectal administration are the known pharmaceutical forms for such administration, such as for example suppositories with cocoa butter or polyethylene glycol bases.

Compositions of the invention suitable for parenteral administration are the known pharmaceutical forms for such administration, for example sterile suspensions in aqueous and oily media or sterile solutions in propylene glycol.

In the compositions of the invention the compounds of formula I may if desired be associated with other compatible pharmacologically active ingredients. For example antacids and acid absorbents such as aluminium hydroxide and magnesium trisilicate may be included in compositions for oral administration to give an immediate antacid effect. Other pharmacologically active agents which may be associated with the compounds of formula I include compounds active on the central nervous system, including short and long acting sedatives such as the barbiturates and methaqualone, antihistaminic and/or antiemetic agents such as cyclizine and diphenhydramine, and anticholinergic agents such as atropine.

Milk and milk solids are valuable in the treatment of peptic ulcer, and the compositions of the invention include liquid and solid compositions based on milk and milk solids.

For maximum stability, the compositions of the invention should preferably have a pH greater than 7; accordingly acidic excipients are not desirable.

In some formulations it may be beneficial to use the compounds of formula I in the form of particles of very small size, such as for example, as obtained by fluid energy milling.

According to another aspect of the invention there is provided a method of treating peptic ulcer which comprises administering to a patient 0.025–2 grams daily of a compound of formula I; in a preferred embodiment of this aspect of the invention, administration is by the oral route.

The starting materials employed in the preparation of compounds of formula I are in many cases known compounds; where they are new, they are prepared by methods analagous to those employed for known compounds, and as such will be apparent to those skilled in the art. By way of example the preparation of some new intermediates is given below.

Preparation I

A solution of 9-formamidoxanthen (30.5 g.) in tetrahydrofuran (400 ml.) was added to a suspension of lithium aluminium hydride (5.2 g.) in tetrahydrofuran (100 ml.) at room temperature. The mixture was stirred and refluxed for 5 hours, left to stand at room temperature overnight and then decomposed by the addition of water (5.2 ml.), 5N sodium hydroxide solution (4 ml.) and water (16.8 ml.). The suspension was filtered, the solid was washed with ether, and the combined filtrate and washings were evaporated. The residual syrup was dissolved in ether and extracted into 3N acetic acid solution (500 ml.) at 5° – 10°C. The aqueous extract was basified, the oil which separated was collected in ether and the dried, ethereal extract was evaporated. The residue was distilled to give 9-methylaminoxanthen, b.p. (bath) 110°C./0.1 mm.

Similarly 9-acetamidoxanthen was reduced to give 9-ethylaminoxanthen, b.p. 137°–140°C/0.9 mm.

EXAMPLE 1

Ethyl isocyanate (1 ml.) was added to a solution of 9-methylaminoxanthen (2.02 g.) in methylene chloride (10 ml.). There was an exothermic reaction and after 20 minutes at room temperature the solvent was evaporated. The residue was recrystallised from benzene to give N'-ethyl-N-methyl-N-9-xanthenylurea, m.p. 139°–141°C.

In a similar manner the following compounds are prepared:

N,N'-dimethyl-N-9-xanthenylurea, m.p. 170°–172°C.
N-methyl-N'-propyl-N-9-xanthenylurea, m.p. 124°–126°C.
N'-t-butyl-N-methyl-N-9-xanthenylurea, m.p. 126°–127°C.
N'-acetyl-N-methyl-N-9-xanthenylurea, m.p. 142°–143°C.
N'-(2-acetoxyethyl)-N-methyl-N-9-xanthenylurea, m.p. 107°–108°C.
N-ethyl-N'-methyl-N-9-xanthenylurea, m.p. 118°–120°C.
N'-(2-ethoxyethyl)-N-methyl-N-9-xanthenylurea, m.p. 89°–90°C.
N'-(2-acetoxyethyl)-N-methyl-N-(2-methyl-9-xanthenyl)urea
N'-acetyl-N-(2-methoxy-9-xanthenyl)-N-methylurea
N'-(2-methoxyethyl)-N-(2-methoxy-9-xanthenyl)-N-methylurea

EXAMPLE 2

Methyl isocyanate (25 ml.) was slowly added to a solution of xanthydrol (30 g.) and triethylamine (1 ml.) in benzene (120 ml.) at 65°C. The solution was kept at 55°C. until evolution of carbon dioxide ceased, refluxed for 1½ hours, cooled and filtered. The solid was collected and recrystallised from benzene to give N,N'-dimethyl-N-9-xanthenylurea solvated with 2 molecules of benzene, m.p. 170°–171°C.

The solvate was dried to constant weight at 95°C./2 mm. to give N,N'-dimethyl-N-9-xanthenylurea, m.p. 173°–174.5°C.

In a similar manner there was prepared:
N,N'-dimethyl-N-(2-chloro-9-xanthenyl)urea, m.p. 156°–159°C.

The following compounds were prepared similarly from the appropriate xanthydrol and isocyanate but using methylene chloride as the reaction solvent at room temperature:

N,N'-diethyl-N-9-xanthenylurea, m.p. 125°–127°C
N,N'-dimethyl-N-(1-methyl-9-xanthenyl)urea, m.p. 171°–172°C
N-(2-fluoro-9-xanthenyl)-N,N'-dimethylurea, m.p. 172°–174°C
N-(1-chloro-9-xanthenyl)-N,N'-dimethylurea, m.p. 202°–206°C
N,N'-dimethyl-N-(4-methyl-9-xanthenyl)urea, m.p. 161°–163°C
N,N'-dimethyl-N-(1-fluoro-9-xanthenyl)urea, m.p. 211°–212°C
N,N'-dimethyl-N-(2-methoxy-9-xanthenyl)urea, m.p. 128°–129.5°C

EXAMPLE 3

A solution of 9-methylaminoxanthen (5 g.) in dry benzene (10 ml.) was added slowly to a stirred solution of silicon tetraisocyanate (1.16 g.) in benzene (10 ml.). The resulting solution was refluxed for 45 minutes and then evaporated to dryness in vacuo. The residue was refluxed for 30 minutes with 90% isopropanol (20ml.), filtered and the filtrate evaporated to dryness. The residue was washed with cold acetone and recrystallised from ethanol to give N-methyl-N-9-xanthenylurea, m.p. 199°–202°C.

In a similar manner the following compound is prepared:

N-(1-fluoro-9-xanthenyl)-N-methylurea

EXAMPLE 4

A mixture of xanthydrol (2 g.), N,N'-dimethylurea (1 g.), toluene (15 ml.) and acetic acid (0.6 ml.) was refluxed for 20 minutes, evaporated to dryness, the residue was washed with water and dried. It was recrystallised from benzene and the crystals dried at 90°C./2mm. to give N,N'-dimethyl-N-9-xanthenylurea, m.p. 169°–170°C.

In a similar manner the following compound is prepared:

N-(1-methoxy-9-xanthenyl)-N,N'-dimethylurea, m.p. 178°–180°C

EXAMPLE 5

N'-2-Acetoxyethyl-N-methyl-N-9-xanthenylurea (2.1 g.), methanol (20 ml.) and potassium cyanide (50 mg.) were refluxed for 20 minutes and then evaporated to dryness. Recrystallisation of the residue from benzene and then from methylene chloride gave N'-(2-hydroxyethyl)-N-methyl-N-9-xanthenylurea as a hydrate, m.p. 130°–132°C.

In a similar manner the following compound is prepared:

N'-(2-hydroxyethyl)-N-methyl-N-(2-methyl-9-xanthenyl)urea

EXAMPLE 6

In the preparation of tablets, mixtures of the following type may be tabletted in conventional manner:

| compound of formula I | 10–90% |
|---|---|
| calcium phosphate | 0–80% |
| maize starch | 5–10% |
| magnesium stearate | ca.1% |
| microcrystalline cellulose | 0–90% |
| | (by weight) |

EXAMPLE 7

The following mixture was formed into tablets in conventional manner, each tablet containing 50 mg. of active ingredient:

| | |
|---|---|
| N,N'-dimethyl-N-9-xanthenylurea | 25% |
| maize starch | 10% |
| calcium phosphate | 20% |
| magnesium stearate | 1% |
| microcrystalline | to 100% by weight |

EXAMPLE 8

In the preparation of enteric coated tablets, tablets prepared as described in Example 7 were coated with sanderac varnish and then coated with cellulose acetate phthalate using a solution of 20% cellulose acetate phthalate and 3% diethyl phthalate in a mixture of equal parts of industrial alcohol and acetone.

EXAMPLE 9

In the preparation of tablets, the following mixture was dry granulated and compressed in a tabletting machine to give tablets containing 5 mg. of active ingredient:

| | |
|---|---|
| N,N'-dimethyl-N-9-xanthenylurea | 10 g. |
| lactose | 5 g. |
| calcium phosphate | 5 g. |
| maize starch | 5 g. |

EXAMPLE 10

In the preparation of enteric coated tablets, the tablets described in Example 9 were given a thin coat of shellac varnish followed by 20 coats of cellulose acetate phthalate.

EXAMPLE 11

In the preparation of capsules, a mixture of the ingredients described in Example 9 was encapsulated in hard gelatin capsules. Enteric coating was applied by conventional dipping in cellulose acetate phthalate.

EXAMPLE 12

The following mixture was compressed into tablets in a conventional manner:

| | |
|---|---|
| N,N'-dimethyl-N-9-xanthenylurea | 25% |
| sodium bicarbonate | 75% |
| peppermint oil | q.s. |

EXAMPLE 13

In the preparation of capsules, a mixture of equal parts by weight of N,N'-dimethyl-N-9-xanthenylurea and calcium phosphate was encapsulated in hard gelatin capsules, each capsule containing 50 mg. of N,N'-dimethyl-N-9-xanthenylurea.

EXAMPLE 14

In the preparation of enteric coated capsules, the capsules of Example 13 were coated with cellulose acetate phthalate in conventional manner.

EXAMPLE 15

Suppositories weighing 1 g. and containing 50 mg. of N,N'-dimethyl-N-9-xanthenylurea were prepared in conventional manner using a base consisting of:

| | |
|---|---|
| polyethylene glycol 4000 | 33% |
| polyethylene glycol 6000 | 47% |
| water | 20% |

EXAMPLE 16

A solution for parenteral administration was prepared by dissolving 100 mg. of N,N'-dimethyl-N-9-xanthenylurea in 2 ml. of propylene glycol and sterilised by filtration.

Compositions similar to those described in Examples 6–16 were also prepared, containing the other preferred compounds described previously in place of N,N'-dimethyl-N-9-xanthenylurea.

We claim:

1. A therapeutic composition having anti-secretory use which comprises as an active ingredient an effective anti-secretory amount of a compound of the Formula $$\text{H} \underset{\underset{O}{\big|}}{\overset{R_1}{\big|}} N - CO - NHR_2 \quad R_o$$

I in which
$R_o$ is selected from the group consisting of hydrogen, halogen, alkyl and alkoxy;
$R_1$ is alkyl; and
$R_2$ is selected from the group consisting of hydrogen, alkyl, hydroxyalkyl, alkanoyloxyalkyl, alkoxyalkyl and alkanoyl; and
wherein the terms "alkyl", "alkoxy", "alkanoyloxy" and "alkanoyl" indicate such groups containing up to 7 carbon atoms, in association with pharmaceutical excipients known for the production of compositions suitable for oral, rectal or parenteral administration.

2. The composition of claim 1 adapted for oral administration and in the form of tablets or capsules.

3. The composition of claim 2 wherein said tablets or capsules are enteric coated.

4. The composition of claim 2 or 6 wherein said tablets or capsules contain 25–500 mg. of said active ingredient.

5. The composition of claim 1 adapted for rectal administration and in the form of suppositories.

6. The composition of claim 3 adapted for parenteral administration and in the form of sterile solutions or suspensions in a liquid carrier.

7. The composition of claim 1 which comprises 0.1–90% by weight of active ingredient.

8. A therapeutic composition having anti-secretory use in dosage unit tablet or capsule form comprising N,N'-dimethyl-N-9-xanthenylurea, and excipients known for the production of pharmaceutical tablets or capsules, said tablets or capsules containing 25 – 500 mg. of said active ingredient and being enteric coated.

9. A method of treating peptic ulcer which comprises administering to a patient in need of said treatment 0.025 – 2 g. daily of a active compound as defined in claim 1.

10. A method of treating peptic ulcers which comprises administering to a patient in need of said treatment an effective amount of a compound as defined in claim 1.

11. The method of claim 10 wherein the compound is N,N'-dimethyl-N-9-xanthenylurea.

12. The method of claim 11 wherein the amount of the active compound administered is 0.025–2 g. daily.

* * * * *